(12) United States Patent
Cannell et al.

(10) Patent No.: US 8,703,109 B2
(45) Date of Patent: Apr. 22, 2014

(54) PROTECTION OF KERATINOUS FIBERS USING CERAMIDES AND/OR GLYCOCERAMIDES

(75) Inventors: David W. Cannell, Plainfield, NJ (US); Jean-Marc Ascione, New York, NY (US)

(73) Assignee: L'Oreal, Paris (FR)

( * ) Notice: Subject to any disclaimer, the term of this patent is extended or adjusted under 35 U.S.C. 154(b) by 942 days.

(21) Appl. No.: 12/058,119

(22) Filed: Mar. 28, 2008

(65) Prior Publication Data

US 2009/0081148 A1    Mar. 26, 2009

Related U.S. Application Data

(63) Continuation of application No. 09/648,376, filed on Aug. 25, 2000, now abandoned.

(51) Int. Cl.
*A61K 8/00* (2006.01)
*A61Q 5/00* (2006.01)
*A61Q 5/12* (2006.01)
*A61K 8/02* (2006.01)

(52) U.S. Cl.
USPC ............... 424/70.19; 424/401; 424/70.21; 424/70.27; 424/70.28

(58) Field of Classification Search
USPC ............ 424/70.27, 401, 70.19, 70.21, 70, 27
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 10/1946 | Bock et al. |
| 2,961,347 A | 11/1960 | Floyd |
| 3,206,462 A | 9/1965 | McCarty |
| 3,227,615 A | 1/1966 | Korden |
| 3,589,578 A | 6/1971 | Kamphausen |
| 3,632,559 A | 1/1972 | Matter et al. |
| 3,836,537 A | 9/1974 | Boerwinkle et al. |
| 3,874,870 A | 4/1975 | Green et al. |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,131,576 A | 12/1978 | Iovine et al. |
| 4,157,388 A | 6/1979 | Christiansen |
| 4,165,367 A | 8/1979 | Chakrabarti |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,240,450 A | 12/1980 | Grollier et al. |
| 4,349,532 A | 9/1982 | Vanlerberghe et al. |
| 4,591,610 A | 5/1986 | Grollier |
| 4,702,906 A | 10/1987 | Jacquet et al. |
| 4,719,282 A | 1/1988 | Nadolsky et al. |
| 4,761,273 A | 8/1988 | Grollier et al. |
| 4,839,166 A | 6/1989 | Grollier et al. |
| 4,996,059 A | 2/1991 | Grollier et al. |
| 5,089,252 A | 2/1992 | Grollier et al. |
| 5,612,025 A | 3/1997 | Cauwet-Martin et al. |
| 5,618,523 A | 4/1997 | Zysman et al. |
| 5,656,258 A | 8/1997 | Cauwet et al. |
| 5,660,818 A | 8/1997 | Dubief et al. |
| 5,661,118 A | 8/1997 | Cauwet et al. |
| 5,679,357 A | 10/1997 | Dubief et al. |
| 5,700,456 A | 12/1997 | Dubief et al. |
| 5,958,392 A | 9/1999 | Grollier et al. |
| 6,951,378 B1 | 10/2005 | Yamada et al. |
| 2001/0031270 A1 | 10/2001 | Douin et al. |

FOREIGN PATENT DOCUMENTS

| | | |
|---|---|---|
| DE | 197 51 550 | 7/1999 |
| DE | 299 04 626 | 2/2000 |
| EP | 0 122 324 | 10/1984 |
| EP | 278 505 | 8/1988 |
| EP | 0 337 354 | 10/1989 |
| EP | 0 557 203 | 8/1993 |
| EP | 659 405 | 6/1995 |
| EP | 672 409 | 9/1995 |
| EP | 739 620 | 10/1996 |
| EP | 739 625 | 10/1996 |
| EP | 1 120 103 | 8/2001 |
| FR | 1 400 366 | 4/1965 |
| FR | 1 492 597 | 7/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 252 840 | 6/1975 |
| FR | 2 270 846 | 12/1975 |
| FR | 2 280 361 | 2/1976 |
| FR | 2 316 271 | 1/1977 |

(Continued)

*Primary Examiner* — Shengjun Wang

(74) *Attorney, Agent, or Firm* — The Marbury Law Group, PLLC

(57) ABSTRACT

The present invention relates to a composition for the protection of keratinous fibers containing at least one compound chosen from ceramides and glycoceramides, at least one cationic polymer, and at least one amphoteric polymer; to a process and kit for protecting keratinous fibers from damage caused by chemical treatment by applying, prior to chemical treatment, to the keratinous fibers a leave-in composition comprising at least one compound chosen from ceramides and glycoceramides.

11 Claims, No Drawings

(56) References Cited

FOREIGN PATENT DOCUMENTS

| | | |
|---|---|---|
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 673 179 | 8/1992 |
| GB | 1 331 819 | 9/1973 |
| GB | 1 347 051 | 2/1974 |
| GB | 1 479 786 | 7/1977 |
| GB | 1 546 809 | 5/1979 |
| WO | WO 93/02656 | 2/1993 |
| WO | WO 97/15271 | 5/1997 |
| WO | WO 97/15272 | 5/1997 |
| WO | WO 97/15273 | 5/1997 |
| WO | WO 97/15274 | 5/1997 |
| WO | WO 97/42281 | 11/1997 |
| WO | WO 99/33444 | 7/1999 |
| WO | WO 00/28966 | 5/2000 |

PROTECTION OF KERATINOUS FIBERS USING CERAMIDES AND/OR GLYCOCERAMIDES

This is a continuation of U.S. patent application Ser. No. 09/648,376, filed Aug. 25, 2000, now abandoned which is incorporated herein by reference.

The present invention relates to a composition for the protection of keratinous fibers containing at least one compound chosen from ceramides and glycoceramides, at least one cationic polymer, and at least one amphoteric polymer. The invention also relates to a process of protecting keratinous fibers using a leave-in composition containing at least one compound chosen from ceramides and glycoceramides.

It is well-known that keratinous fibers, particularly human hair, are damaged, i.e., sensitized or weakened, to various degrees by the action of atmospheric agents and by the action of various chemical hair treatments such as dyeing, bleaching, permanent waving, or relaxing/straightening, especially by the repeated use of such chemical treatments over time. The hair then becomes difficult to detangle and to style and also becomes rough to the touch.

To protect the hair during chemical treatment, it is known to include various protective compounds in the chemical treatment compositions. Ceramides are known as protective agents for the hair, but they can have the drawback of being sometimes unstable in alkaline formulations. This can be a problem because chemical treatments for hair, such as dyeing, bleaching, permanent waving, or relaxing/straightening, are generally alkaline. The instability can cause particular difficulties in shelf-life and storage for the chemical treatment compositions containing ceramide protecting agents. Thus, it would be desirable to use ceramides as protecting agents for hair without compromising the stability of the chemical treatment formulations with which they are used.

In addition to protection, it is also desirable to provide the hair with desirable styling properties, appearance and feel following chemical treatment. Cationic polymers have been used to facilitate detangling and improve the softness and feel of the hair, and also to provide protection to the hair fibers. However, cationic polymers can have a number of disadvantages when used alone, such as a possible tendency to make the hair appear lank and greasy, particularly when other chemical treatments are superposed on the hair. Amphoteric polymers have also been used but similarly fail to provide sufficient softness and detanglement when used on their own.

Thus, there is a need for stable compositions which protect the hair from damage caused by chemical treatment and which can also allow the hair to retain excellent styling properties, feel, and appearance.

The present inventors have discovered, surprisingly, that applying a composition containing at least one compound chosen from ceramides and glycoceramides to the keratinous fibers prior to chemical treatment, i.e., as a pre-treatment composition, can improve the protection of the fibers from the ravages of the chemical treatments. In other words, problems of instability may be avoided by not including the at least one compound chosen from ceramides and glycoceramides in the treatment composition itself. In one embodiment of the invention, the pre-treatment composition is left on the keratinous fibers, i.e., by not rinsing the fibers prior to chemical treatment. The keratinous fibers may be hair, particularly human hair.

The inventors have also discovered that the combination of at least one compound chosen from ceramides and glycoceramides, at least one cationic polymer, and at least one amphoteric polymer forms a composition which can, in certain embodiments of the invention, provide superior protection, feel, and an overall healthy appearance to keratinous fibers subjected to chemical treatment.

Consequently, one subject of the present invention is a composition for the protection of keratinous fibers, comprising at least one compound chosen from ceramides and glycoceramides, at least one cationic polymer, and at least one amphoteric polymer.

Another subject of the present invention is a process for protecting keratinous fibers by applying to the keratinous fibers a leave-in composition comprising at least one compound chosen from ceramides and glycoceramides and then applying a chemical treatment such as a dyeing composition, a bleaching composition, a relaxing composition, or a permanent waving composition. The composition may further comprise at least one polymer chosen from at least one cationic polymer and at least one amphoteric polymer.

Yet another subject of the present invention is a multi-compartment kit for the chemical treatment of keratinous fibers having at least two separate compartments, wherein a first compartment contains a composition comprising at least one compound chosen from ceramides and glycoceramides, and a second compartment contains a composition for chemical treatment of the fibers, e.g., dyeing, bleaching, permanent waving, or relaxing. The first compartment may also contain at least one polymer chosen from at least one cationic polymer and at least one amphoteric polymer Other subjects of the invention will become apparent on reading the detailed description and the examples which follow.

Ceramides and Glycoceramides

Ceramide and/or glycoceramide compounds which may be used in the inventive composition may be chosen from natural and synthetic ceramides, natural and synthetic glycoceramides, natural and synthetic pseudoceramides and natural and synthetic neoceramides.

Representative natural or synthetic ceramide or glycoceramide compounds which may be used according to the present invention include those of the following formula (I):

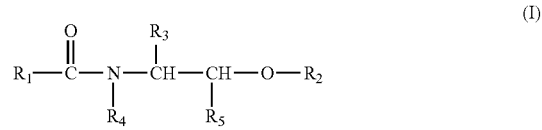

in which:

$R_1$ is chosen from:

linear and branched, saturated and unsaturated, $C_5$-$C_{50}$ hydrocarbon radicals, wherein the hydrocarbon radicals may be substituted with at least one hydroxyl group, the at least one hydroxyl group being optionally esterified with an acid $R_6COOH$ wherein $R_6$ is chosen from saturated and unsaturated, linear and branched $C_1$-$C_{35}$ hydrocarbon radicals which may be monohydroxylated or polyhydroxylated, and further wherein when the hydrocarbon radicals of $R_6$ are mono- or polyhydroxylated, the hydroxyl group(s) may be esterified with a compound chosen from saturated and unsaturated, linear and branched $C_1$-$C_{35}$ fatty acids which may be monohydroxylated or polyhydroxylated, R"—(NR—CO)—R' radicals, wherein R is chosen from a hydrogen atom and mono- and polyhydroxylated, e.g., mono-hydroxylated, $C_1$-$C_{20}$ hydrocarbon radicals, and R' and R" are chosen from hydrocarbon radicals in which the sum of the carbon atoms ranges from 9 to 30, R' being a divalent radical, and $R_7$—O—CO—$(CH_2)_a$ radicals, wherein $R_7$ is chosen from $C_1$-$C_{20}$ hydrocarbon radicals and a is an integer ranging from 1 to 12;

$R_2$ is chosen from a hydrogen atom and (glycosyl)$_b$, (galactosyl)$_c$, sulphogalactosyl, phosphorylethylamine and phosphorylethylammonium radicals, wherein b is an integer ranging from 1 to 4 and c is an integer ranging from 1 to 8;

$R_3$ is chosen from a hydrogen atom and saturated and unsaturated, hydroxylated and non-hydroxylated $C_1$-$C_{33}$ hydrocarbon radicals, it being possible for the hydroxylated hydrocarbon radical(s) to be esterified with an acid chosen from inorganic acids and organic acids of the formula $R_6COOH$, wherein $R_6$ is defined above, it also being possible for the hydroxylated hydrocarbon radical(s) to be etherified with a radical chosen from (glycosyl)$_b$, (galactosyl)$_c$, sulphogalactosyl, phosphorylethylamine and phosphorylethylammonium radicals, wherein b and c are defined above, and it also being possible for $R_3$ to be substituted with at least one $C_1$-$C_{14}$ alkyl radical;

In one embodiment, $R_3$ is chosen from $C_{15}$-$C_{26}$ α-hydroxyalkyl radicals wherein the hydroxyl group may optionally be esterified with a $C_{16}$-$C_{30}$ α-hydroxy acid.

$R_4$ is chosen from a hydrogen atom, methyl radicals, ethyl radicals, saturated and unsaturated, linear and branched, optionally hydroxylated $C_3$-$C_{50}$ hydrocarbon radicals and radicals —$CH_2$—CHOH—$CH_2$—O—$R_8$ in which $R_8$ is chosen from $C_{10}$-$C_{26}$ hydrocarbon radicals and radicals $R_7$—O—CO—$(CH_2)_a$, $R_7$ being chosen from $C_1$-$C_{20}$ hydrocarbon radicals and a being an integer ranging from 1 to 12;

$R_5$ is chosen from a hydrogen atom and saturated and unsaturated, linear and branched, optionally mono- and polyhydroxylated $C_1$-$C_{30}$ hydrocarbon radicals, it being possible for the hydroxyl radical(s) to be etherified with a radical chosen from (glycosyl)$_b$, (galactosyl)$_c$, sulphogalactosyl, phosphorylethylamine and phosphorylethylammonium radicals, wherein b and c are defined above; with the proviso that when $R_3$ and $R_5$ are a hydrogen atom or when $R_3$ is a hydrogen atom and $R_5$ is a methyl radical, then $R_4$ is not a hydrogen atom or a methyl or ethyl radical.

Among the compounds of formula (I) above, one of ordinary skill in the art may choose the ceramides and/or glycoceramides whose structures are described by Downing, Journal of Lipid Research, Vol. 35 (1994), pages 2060-2068, or those described in French patent application FR-2,673,179, and the disclosures of which are incorporated by reference. The structures of these ceramides and/or glycoceramides may be chosen from the seven ceramide structures shown below:

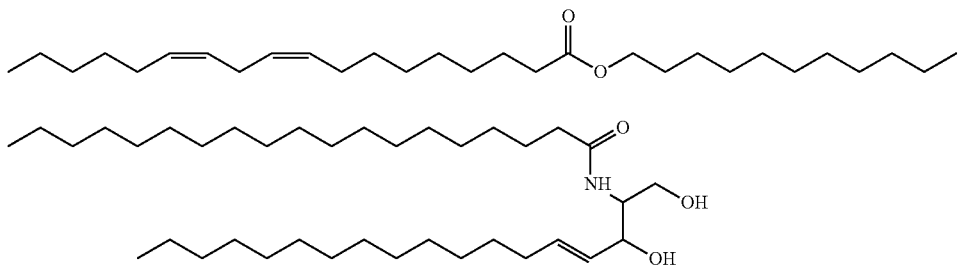

Type 1

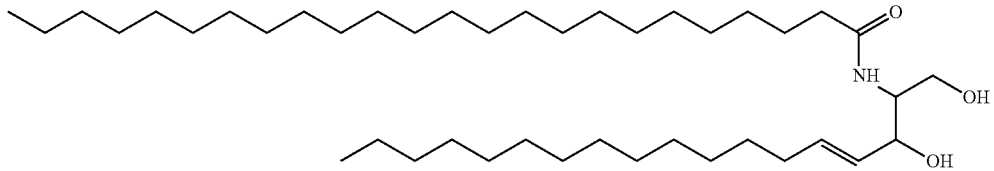

Type 2

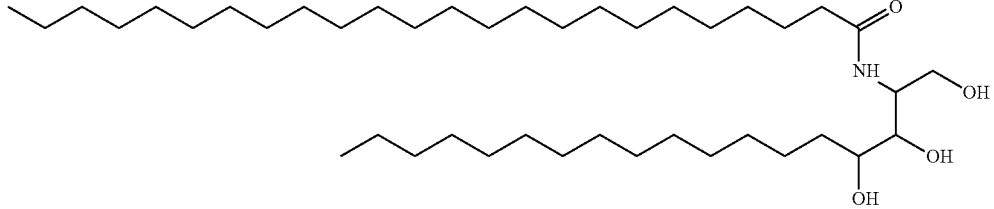

Type 3

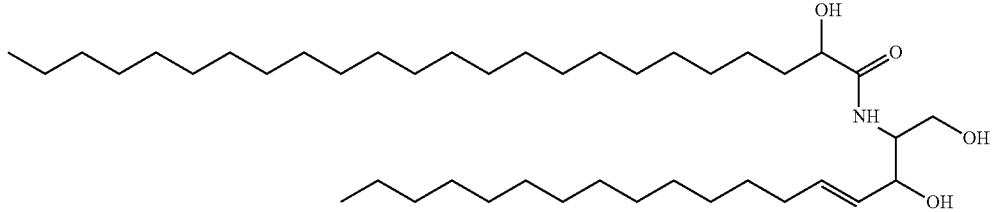

Type 4

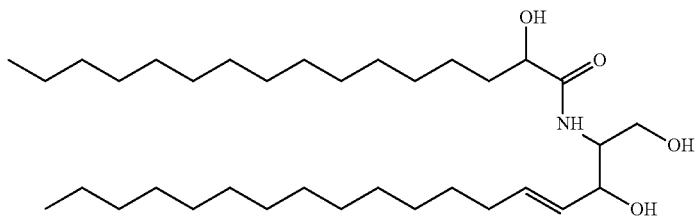

Type 5

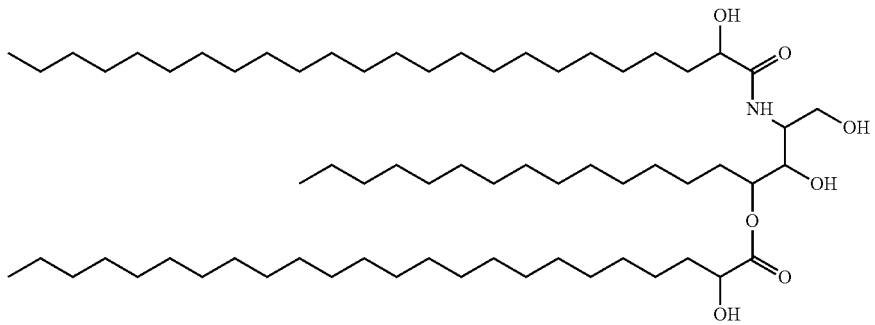

Type 6 I

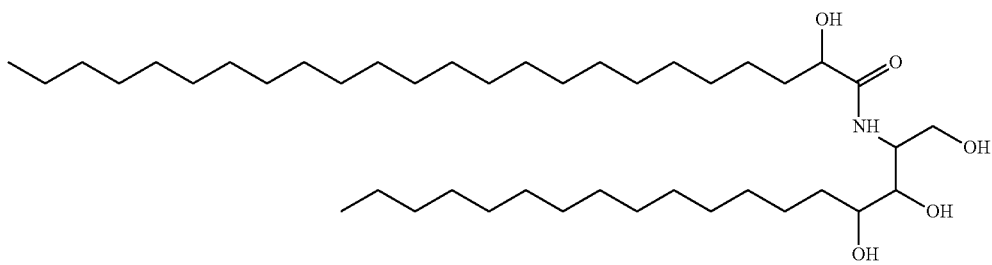

Type 6 II

The ceramide and/or glycoceramide compounds according to the invention may be chosen from compounds of formula (I) in which $R_1$ is chosen from optionally hydroxylated, saturated and unsaturated alkyl radicals derived from $C_{14}$-$C_{22}$ fatty acids; $R_2$ is a hydrogen atom; and $R_3$ is chosen from optionally hydroxylated linear, saturated $C_{11}$-$C_{17}$ radicals, for example, $C_{13}$-$C_{15}$ radicals.

Such compounds are, for example:
N-linoleoyldihydrosphingosine,
N-oleoyldihydrosphingosine,
N-palmitoyldihydrosphingosine,
N-stearoyldihydrosphingosine,
N-behenoyldihydrosphingosine,
N-2-hydroxypalmitoyldihydrosphingosine,
N-stearoylphytosphingosine,
N-palmitamidohexadecanediol,
2-oleamido-1,3-octadecanediol,
and mixtures of these compounds.

In another embodiment, the ceramide may be chosen from 2-oleamido-1,3-octadecanediol (its CTFA name), sold, for example, as MEXANYL GZ by Chimex, and N-2-hydroxypalmitoyldihydrosphingosine (CTFA name hydroxypalmitoylsphinganine), sold, for example, as MEXANYL GAA by Chimex.

The at least one compound chosen from ceramides and glycoceramides is generally present in the inventive composition in an amount effective for providing improved protection to keratinous fibers. In one embodiment, the at least one compound chosen from ceramides and glycoceramides is generally present in an amount ranging from about 0.0005 to about 2% by weight relative to the total weight of the composition. In another embodiment, the at least one compound chosen from ceramides and glycoceramides is generally present in the inventive composition in an amount ranging from about 0.001 to about 1% by weight relative to the total weight of the composition.

Cationic Polymers

For the purposes of the present invention, the expression "cationic polymer" denotes any polymer containing cationic groups and/or groups that can be ionized into cationic groups.

The cationic polymers, which may be used in accordance with the present invention, may be chosen from, for example, those described in European patent applications EP-A-337354 and EP-A-557203 and in French Patent Nos. 2,270,846, 2,383,660, 2,598,611, 2,470,596 and 2,519,863.

Cationic polymers to be used in the present inventive composition may be chosen from those which contain monomer units comprising amine groups chosen from primary, secondary, tertiary and quaternary amine groups, wherein the amine groups may either form part of the main polymer chain or may be borne by a side substituent directly linked thereto.

The cationic polymers used may generally have a number-average molecular mass ranging from about 500 to about 5,000,000, or, in another embodiment, ranging from about 1000 to about 3,000,000.

Among the cationic polymers which may be used in the inventive composition are polymers such as polyamine, polyamino amide and polyquaternary ammonium polymers. These types of polymers are described, for example, in French Patent Nos. 2,505,348 or 2,542,997. Such polymers may include, but are not limited to polymers in the families (1) to (14) below:

(1) homopolymers and copolymers derived from at least one monomer chosen from acrylic and methacrylic esters and amides and/or comprising at least one of the units of formula (II), (III), (IV) or (V) below:

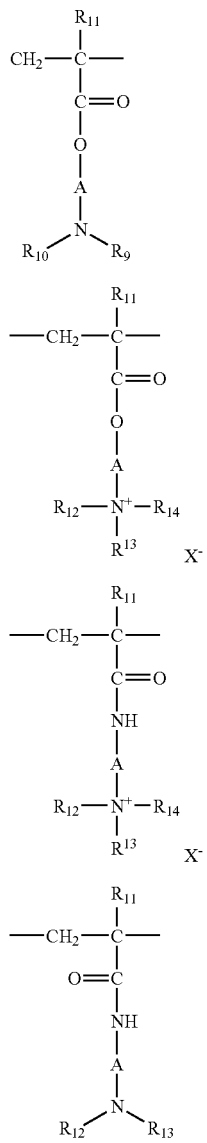

in which:

A, which may be identical or different, is chosen from linear and branched alkyl groups of 1 to 6 carbon atoms, for example 2 or 3 carbon atoms. The linear and branched alkyl groups may, for example, be chosen from hydroxyalkyl groups having 1 to 4 carbon atoms;

$R_9$ and $R_{10}$, which may be identical or different, are chosen from hydrogen and alkyl groups containing from 1 to 6 carbon atoms, for example methyl or ethyl;

$R_{11}$, which may be identical or different, are chosen from a hydrogen atom and a methyl radical;

$R_{12}$, $R_{13}$ and $R_{14}$, which may be identical or different, are chosen from alkyl groups containing from 1 to 18 carbon atoms, for example, 1 to 6 carbon atoms, and a benzyl radical;

$X^-$ is an anion derived from acids chosen from inorganic and organic acids, such as a methosulphate anion, or a halide, such as chloride or bromide.

The polymers of the family (1) may also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic and methacrylic acids and esters of said acids, vinyllactams, such as vinylpyrrolidone and vinylcaprolactam, and vinyl esters.

Thus, among these polymers of family (1) which may be mentioned are copolymers of acrylamide and of dimethylaminoethyl methacrylate quaternized with dimethyl sulphate or with a dimethyl halide, such as those sold under the name HERCO-FLOC by Hercules.

copolymers of acrylamide and of methacryloyloxyethyltrimethylammonium chloride described, for example, in patent application EP-A-080976, and sold, for example, under the name BINA QUAT P 100 by Ciba Geigy.

the copolymer of acrylamide and of methacryloyloxyethyltrimethylammonium methosulphate, such as those sold by Hercules under the name RETEN.

quaternized or non-quaternized vinylpyrrolidone/dialkylaminoalkyl acrylate or methacrylate copolymers, such as those sold by ISP under the GAFQUAT name, e.g., GAFQUAT 734 or GAFQUAT 755, or under the product names COPOLYMER 845, 958 and 937. These polymers are described in detail in French Patent Nos. 2,077,143 and 2,393,573.

dimethylaminoethyl methacrylate/vinylcaprolactam/vinylpyrrolidone terpolymers, such as those sold by ISP under the name GAFFIX VC 713.

vinylpyrrolidone/methacrylamidopropyldimethylamine copolymers, sold, for example, by ISP under the name STYLEZE CC 10, and quaternized vinylpyrrolidone/dimethylaminopropylmethacrylamide copolymers, such as those sold by ISP under the name GAFQUAT HS 100.

(2) The cellulose ether derivatives containing quaternary ammonium groups, described in French Patent No. 1,492,597, and sold, for example, by Union Carbide under the denominations "JR" (JR 400, JR 125, JR 30M) or "LR" (LR 400, LR 30M). These polymers are also defined in the CTFA dictionary as quaternary ammoniums of hydroxyethylcellulose which has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt. Commercial products corresponding to this definition include CELQUAT L 200 and CELQUAT H 100, sold by National Starch.

(4) The cationic polysaccharides described more particularly in U.S. Pat. Nos. 3,589,578 and 4,031,307, such as guar gums containing cationic trialkylammonium groups. Guar gums modified with a salt (e.g., chloride) of 2,3-epoxypropyltrimethylammonium are used, for example. Such products are sold, for example, by Meyhall under the "JAGUAR" name, e.g., JAGUAR C 15, JAGUAR C 17, and JAGUAR C162.

(5) Polymers comprising piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French Patent Nos. 2,162,025 and 2,280,361.

(6) Water-soluble polyamino amides prepared in particular by polycondensation of an acidic compound with a polyamine. These polyamino amides may be crosslinked with an epihalohydrin, a diepoxide, a dianhydride, an unsaturated dianhydride, a bis-unsaturated derivative, a bis-halohydrin, a bis-azetidinium, a bis-haloacyidiamine, a bis-alkyl halide or alternatively with an oligomer resulting from the reaction of a difunctional compound which is reactive with a bis-halohydrin, a bis-azetidinium, a bis-haloacyidiamine, a bis-alkyl halide, an epihalohydrin, a diepoxide or a bis-unsaturated derivative. The crosslinking agent is used in proportions ranging from about 0.025 to about 0.35 mol per amine group of the polyamino amide. These polyamino amides may be alkylated or, if they contain one or more tertiary amine functions, they may be quaternized. Such polymers are described, in particular, in French Patent Nos. 2,252,840 and 2,368,508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and may be, for example, methyl, ethyl or propyl. Such polymers are described in particular in French Patent No. 1,583,363.

Among these derivatives, mention may be made more particularly of the adipic acid/dimethylaminohydroxypropyl/diethylenetriamine polymers sold under the name CARTARETINE F, F4 or F8 by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio of the polyalkylene polyamine to the dicarboxylic acid ranges from about 0.8:1 to about 1.4:1. The polyamino amide resulting therefrom is reacted with epichlorohydrin in a molar ratio of epichlorohydrin relative to the secondary amine group of the polyamino amide ranging from about 0.5:1 to about 1.8:1. Such polymers are described in particular in U.S. Pat. Nos. 3,227,615 and 2,961,347 and are sold, for example, by Hercules, Inc. under the name HERCOSETT 57 or under the name PD 170 or DELSETTE 101 in the case of the copolymer of adipic acid/epoxypropyl/diethylenetriamine.

(9) Cyclopolymers of alkyldiallylamine or of dialkyldiallylammonium, such as the homopolymers or copolymers containing, as main constituent of the chain, units corresponding to formula (VI) or (VII):

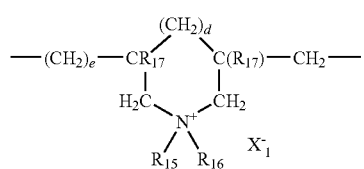

(VI)

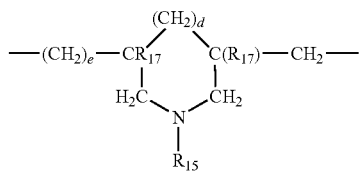

(VII)

in which:
d and e are equal to 0 or 1, the sum d+e being equal to 1;
$R_{17}$ is chosen from a hydrogen atom and a methyl radical;
$R_{15}$ and $R_{16}$, which may be identical or different, are chosen from unsubstituted $C_1$-$C_{22}$ alkyl groups, $C_1$-$C_5$ hydroxyalkyl groups, and $C_1$-$C_4$ amidoalkyl groups, or $R_{15}$ and $R_{16}$ may form, together with the nitrogen atom to which they are attached, heterocyclic groups, such as piperidyl and morpholinyl;
$X_1^-$ is an anion such as bromide, chloride, acetate, borate, citrate, tartrate, bisulphate, bisulphite, sulphate or phosphate.

These polymers are described in particular in French Patent No. 2,080,759 and in its Certificate of Addition No. 2,190,406. Among the polymers defined above, one example is the homopolymer of dimethyldiallyl ammonium chloride sold as MERQUAT 100 by Calgon (and homologues of lower molecular weight) and copolymers of dimethyldiallyl ammonium chloride and acrylamide sold under the name MERQUAT 550, also by Calgon.

(10) The quaternary diammonium polymer containing repeating units corresponding to the formula (VIII):

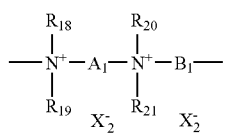

(VIII)

in which:
$R_{18}$, $R_{19}$, $R_{20}$ and $R_{21}$, which may be identical or different, are chosen from aliphatic, alicyclic and arylaliphatic radicals containing from 1 to 20 carbon atoms and $C_1$-$C_4$ hydroxyalkylaliphatic radicals, or alternatively $R_{18}$, $R_{19}$, $R_{20}$ and $R_{21}$, together or separately, constitute, with the nitrogen atoms to which they are attached, heterocycles optionally containing a second heteroatom other than nitrogen, or alternatively $R_{18}$, $R_{19}$, $R_{20}$ and $R_{21}$, which may be identical or different, are chosen from linear and branched ($C_1$-$C_6$) alkyl radicals substituted with at least one substituent chosen from nitrile groups; ester groups; acyl groups; amide groups; and —CO—O—$R_{22}$-D groups and —CO—NH—$R_{22}$-D groups, where $R_{22}$ is an alkylene and D is a quaternary ammonium group;
$A_1$ and $B_1$, which may be identical or different, are chosen from linear and branched, saturated and unsaturated polymethylene groups containing from 2 to 20 carbon atoms, and which may contain, linked to or intercalated in the main chain, at least one entity chosen from aromatic rings, oxygen and sulphur atoms, and sulphoxide, sulphone, disulphide, amino, alkylamino, hydroxyl, quaternary ammonium, ureido, amide and ester groups, and
$X_2^-$ is an anion chosen from anions derived from acids chosen from inorganic and organic acids and halide anions, such as chloride or bromide.

$A_1$, $R_{18}$ and $R_{20}$ may form, with the two nitrogen atoms to which they are attached, a piperazine ring. In addition, if $A_1$ is chosen from linear and branched, saturated and unsaturated alkylene and hydroxyalkylene radicals, $B_1$ may also be chosen from a group $—(CH_2)_f—CO-E-OC—(CH_2)_f—$ in which:

f is an integer ranging from 1 to 100, e.g., from 1 to 50,

E is chosen from:

a) a glycol residue of formula:

—O-G-O—, where G is chosen from linear and branched hydrocarbon radicals and groups corresponding to one of the following formulae:

$—(CH_2—CH_2—O)_g—CH_2—CH_2—$ $—(CH_2—CH(CH_3)—O)_h—CH_2—CH(CH_3)—$ where g and h are each an integer ranging from 1 to 4, representing a defined and unique degree of polymerization or any number ranging from 1 to 4 representing an average degree of polymerization;

b) a bis-secondary diamine residue such as a piperazine derivative;

c) a bis-primary diamine residue of formula: —NH-J-NH—, where J is chosen from linear and branched hydrocarbon radicals, or alternatively the divalent radical $—CH_2—CH_2—S—S—CH_2—CH_2—$;

d) a ureylene group of formula: —NH—CO—NH—.

These polymers generally may have a number-average molecular mass ranging from about 1,000 to about 100,000.

Polymers of this type are described, for instance, in French Patent Nos. 2,320,330, 2,270,846, 2,316,271, 2,336,434 and 2,413,907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Polymers which may be used in the inventive composition include those comprising repeating units corresponding to formula (IX) below:

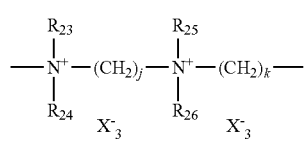

(IX)

in which:

$R_{23}$, $R_{24}$, $R_{25}$ and $R_{26}$, which may be identical or different, are chosen from alkyl and hydroxyalkyl radicals containing from 1 to 4 carbon atoms;

j and k are integers ranging from 2 to 20; and $X_3^-$ is an anion derived from an acid chosen from inorganic and organic acids. Such polymers include polyquaternium-34, sold under the name MEXOMERE PAK by Chimex and hexadimethrine chloride, sold as IONENE G or MEXOMERE PO by Chimex.

(11) Polyquaternary ammonium polymers comprising units of formula (X):

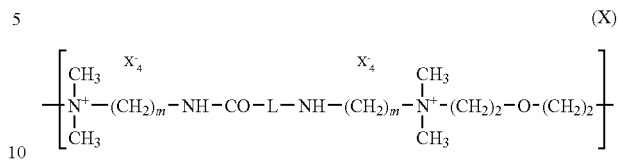

in which:

m is an integer ranging from 1 to 6,

L is an entity chosen from a single bond and $—(CH_2)_n—CO—$ groups in which n is an integer chosen from 4 or 7, and $X_{4-}$ is an anion.

Such polymers can be prepared according to the procedures described in U.S. Pat. Nos. 4,157,388, 4,702,906, and 4,719, 282 and also in EP-A-122324. Among these, one may mention, for example, the products MIRAPOL A15 (polyquaternium-2), MIRAPOL AD1, MIRAPOL AZ1, and MIRAPOL 175 sold by Rhodia.

(12) Quaternary polymers of vinylpyrrolidone and of vinylimidazole, such as those sold by BASF under the names LUVIQUAT FC 905, FC 550, AND FC 370.

(13) Polyamines such as the product referred to under the name polyethylene glycol (15) tallow polyamine in the CTFA dictionary and sold as, for example, POLYQUART H by Henkel.

(14) Crosslinked polymers of methacryloyloxy $(C_1$-$C_4)$ alkyltri$(C_1$-$C_4)$alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with a compound containing olefinic unsaturation, in particular methylenebisacrylamide. It is more particularly possible to use an acrylamide/methacryloyloxyethyltrimethylammonium chloride (20/80 by weight) crosslinked copolymer in the form of a dispersion containing 50% by weight of the said copolymer in mineral oil. This dispersion is sold under the name SALCARE® SC 92 by the company Allied Colloids. It is also possible to use a crosslinked homopolymer of methacryloyloxyethyltrimethylammonium chloride containing about 50% by weight of the homopolymer in mineral oil or in a liquid ester. These dispersions are sold under the names SALCARE® SC 95 and SALCARE® SC 96 by the company Allied Colloids.

Other cationic polymers, which may be used in the context of the invention, are polyalkyleneimines, in particular polyethyleneimines, polymers containing vinylpyridine or vinylpyridinium units, condensates of polyamines and epichlorohydrin, polyquaternary ureylenes and chitin derivatives.

Among the cationic polymers which may be used according to the invention, one may, for example, use polymers of the families (1), (9), (10), (11) and (14), such as:

the polymers of poly(quaternary ammonium) type prepared and described in French Patent No. 2,270,846, comprising repeating units corresponding to formula (XI) below:

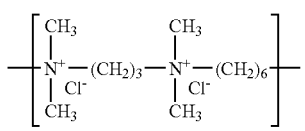

(XI)

and, in one embodiment, those whose weight-average molar mass, determined by gel permeation chromatography, ranges from about 9500 to about 9900;

the polymers of poly(quaternary ammonium) type prepared and described in French Patent No. 2,270,846, comprising repeating units corresponding to the formula (XII) below:

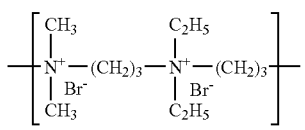

(XII)

and, in one embodiment, those whose weight-average molar mass, determined by gel permeation chromatography, is about 1200.

The cationic polymers of the families (10) and (11) may include hexadimethrine chloride, polyquaternium-2 and polyquaternium-34.

The at least one cationic polymer is generally present in the inventive composition in an amount sufficient to provide improved styling to keratinous fibers, wherein the composition contains at least one compound chosen from ceramides and glycoceramides present in an amount effective for providing improved protection to keratinous fibers. In one embodiment, the at least one cationic polymer may be present in the inventive composition in an amount ranging from about 0.01 to about 5% by weight relative to the total weight of the composition. In another embodiment, the at least one cationic polymer may be present in an amount ranging from about 0.05 to about 2% by weight relative to the total weight of the composition.

Amphoteric Polymers

The amphoteric polymers which can be used in accordance with the present invention can be chosen from polymers containing at least one unit K and at least one unit M, wherein the units K and M are distributed randomly in the polymer chain, in which:

K is chosen from units derived from monomers containing at least one basic nitrogen atom and M is chosen from units derived from acid monomers containing at least one group chosen from carboxylic and sulphonic groups; or K and M, which may be identical or different, may be chosen from units derived from monomers chosen from carboxybetaine and sulphobetaine zwitterionic monomers; or K and M, which may be identical or different, may be chosen from cationic polymer chains containing at least one amine group chosen from primary, secondary, tertiary and quaternary amine groups, in which at least one of the amine groups bears a group chosen from carboxylic and sulphonic groups connected to said amine via a hydrocarbon radical; or K and M form part of a polymer with an α,β-dicarboxyethylene unit, in which one of the carboxyl groups has been reacted with a polyamine containing at least one group chosen from primary and secondary amine groups.

The amphoteric polymers corresponding to the definition given above may be chosen from the following polymers:

(1) polymers resulting from the copolymerization of (a) at least one monomer derived from a vinyl compound bearing a carboxylic group such as acrylic acid, methacrylic acid, maleic acid, α-chloroacrylic acid, with (b) at least one basic monomer derived from a substituted vinyl compound containing at least one basic atom, such as dialkylaminoalkyl methacrylates and acrylates, dialkylaminoalkylmethacrylamides and -acrylamides. Such compounds are described in U.S. Pat. No. 3,836,537. Mention may also be made of the sodium acrylate/acrylamidopropyltrimethylammonium chloride copolymer sold as POLYQUART KE 3033 by Henkel Corp.

The vinyl compound may also be a dialkyldiallylammonium salt such as diethyldiallylammonium chloride. Such copolymers include, for example, the diallyidimethylammonium chloride/acrylic acid (80/20) copolymer sold under the name MERQUAT 280 DRY by the company Calgon (CTFA name: Polyquaternium-22); the dimethyldiallylammonium chloride/acrylic acid (95/5) copolymer sold under the name MERQUAT 295 DRY by the company Calgon (CTFA name: Polyquaternium-22); the copolymer of methacrylamidopropyltrimonium chloride, of acrylic acid and or methyl acrylate, sold under the name MERQUAT 2001 by the company Calgon (CTFA name: Polyquaternium-47); and the acrylamide/dimethyldiallylammonium chloride/acrylic acid terpolymer sold under the name MERQUAT PLUS 3330 DRY by the company Calgon (CTFA name: Polyquaternium-39).

In one embodiment, the copolymer is a diallyidimethylammonium chloride/acrylic acid copolymer.

(2) polymers containing units derived from:

a) at least one monomer chosen from acrylamides and methacrylamides substituted on the nitrogen with an alkyl radical, b) at least one acidic comonomer containing at least one reactive carboxylic group, and c) at least one basic comonomer, such as esters, containing primary, secondary, tertiary and quaternary amine substituents, of acrylic and methacrylic acids and the product of quaternization of dimethylaminoethyl methacrylate with dimethyl or diethyl sulphate.

The N-substituted acrylamides or methacrylamides are groups in which the alkyl radicals contain from 2 to 12 carbon atoms, e.g., N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers may be chosen from acrylic acid, methacrylic acid, crotonic acid, itaconic acid, maleic acid and fumaric acid comonomers and $C_1$ to $C_4$ alkyl monoesters of at least one of maleic acid, fumaric acid, maleic anhydride, and fumaric anhydride.

The basic comonomers may be chosen from aminoethyl, butylaminoethyl, N,N'-dimethylaminoethyl and N-tert-butylaminoethyl methacrylates. For example, the copolymer whose CTFA (4th edition, 1991) name is octylacrylamide/acrylates/butylaminoethyl methacrylate copolymer and is sold under the names AMPHOMER or LOVOCRYL 47 by the company National Starch, may be used.

(3) crosslinked and alkylated polyamino amides partially or totally derived from polyamino amides of formula (XIII):

$$-\!\!\left[\text{CO}-\text{R}_{27}-\text{CO}-\text{Q}\right]\!\!- \qquad \text{(XIII)}$$

in which:

$R_{27}$ is chosen from divalent radicals derived from an entity chosen from saturated dicarboxylic acids; mono- and dicarboxylic aliphatic acids containing an ethylenic double bond; esters of a $C_1$-$C_6$ alkanol of any of these acids; and radicals derived from the addition of any of these acids to an amine chosen from bis(primary) and bis(secondary) amines. The saturated carboxylic acids may be chosen, for example, from acids having from 6 to 10 carbon atoms, such as adipic acid, 2,2,4-trimethyladipic acid and 2,4,4-trimethyladipic acid, terephthalic acid, and acids containing an ethylenic double bond such as, for example, acrylic acid, methacrylic acid and itaconic acid.

Q is chosen from bis(primary), mono- and bis(secondary) polyalkylene-polyamine radicals and may be present in the following proportions:

a) from 60 to 100 mol % of the radical (XIV)

$$-\!\!\left[\text{NH}-(\text{CH}_2)_p-\text{NH}\right]_q\!\!- \qquad \text{(XIV)}$$

where p=2 and q=2 or 3, or alternatively p=3 and q=2, the radical (XIV) being derived from an entity chosen from diethylenetriamine, triethylenetetraamine and dipropylenetriamine;

b) from 0 to 40 mol % of the radical (XIV) where p=2 and q=1 and which is derived from ethylenediamine, or from the radical derived from piperazine:

—N(CH₂CH₂CH₂CH₂)N— c) from 0 to 20 mol % of the radical (XIV) where p=6 and q=1 and which is derived from hexamethylenediamine, wherein the polyalkylene-polyamine radicals Q may be crosslinked by addition of a difunctional crosslinking agent chosen from epihalohydrines, diepoxides, dianhydrides and bis-unsaturated derivatives, generally using from about 0.025 to about 0.35 mol of crosslinking agent per amine group of the polyamino amide and alkylated by the action of an alkylating agent chosen from acrylic acid, chloroacetic acid, alkane sultone, and salts of said alkylating agents. The alkane sultones used in the alkylation may be propane sultone or butane sultone and the salts of the alkylating agents may be the sodium or potassium salts.

(4) polymers containing zwitterionic units of formula (XV):

$$R_{28}\!\!-\!\!\left[\begin{array}{c}R_{29}\\|\\C\\|\\R_{30}\end{array}\right]_r\!\!-\!\!\begin{array}{c}R_{31}\\|\\N^+\\|\\R_{32}\end{array}\!\!-(\text{CH}_2)_s-\overset{\text{O}}{\underset{\|}{\text{C}}}-\text{O}^- \qquad \text{(XV)}$$

in which:

$R_{28}$ is chosen from a polymerizable unsaturated group such as an acrylate, methacrylate, acrylamide or methacrylamide group;

r and s, which may be identical or different, are chosen from an integer ranging from 1 to 3;

$R_{29}$ and $R_{30}$, which may be identical or different, are chosen from a hydrogen atom, and methyl, ethyl and propyl radicals;

$R_{31}$ and $R_{32}$, which may be identical or different, are chosen from a hydrogen atom and alkyl radicals such that the sum of the carbon atoms in $R_{31}$ and $R_{32}$ does not exceed 10.

The polymers comprising such units can also contain units derived from non-zwitterionic monomers such as dimethyl- or diethylaminoethyl acrylate or methacrylate or alkyl acrylates or methacrylates, acrylamides or methacrylamides or vinyl acetate.

By way of example, mention may be made of the copolymer of methyl methacrylate/dimethyl carboxymethylammonio methyl ethylmethacrylate, sold as DIAFORMER Z301 by Sandoz.

(5) polymers, as well as the salts formed by these compounds with bases or acids, derived from chitosan containing monomer units corresponding to formulae (XVI), (XVII) and (XVIII) below:

(XVI) — chitosan unit with NHCOCH₃

(XVII) — chitosan unit with NH₂

(XVIII) — chitosan unit with NH—C(=O)—R₃₃—COOH the unit (XVI) generally being present in proportions ranging from 0 to about 30%, the unit (XVII) generally in proportions of from about 5 to about 50% and the unit (XVIII) generally in proportions of from about 30 to about 90%, it being understood that, in unit (XVIII), $R_{29}$ is chosen from a radical of formula (XIX):

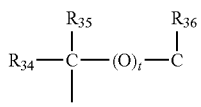

in which:

if t=0, each of $R_{34}$, $R_{35}$ and $R_{36}$, which may be identical or different, is chosen from a hydrogen atom, a methyl radical, a hydroxyl radical, an acetoxy radical, an amino residue, and a monoalkylamine residue and a dialkylamine residue which are optionally interrupted by at least one nitrogen atom and/or optionally substituted with at least one substituent chosen from amine groups, hydroxyl groups, carboxyl groups, alkylthio groups, sulphonic groups, alkylthio residues in which the alkyl group bears an amino residue, and wherein at least one of the radicals $R_{34}$, $R_{35}$ and $R_{36}$ is a hydrogen atom, or, if t=1, each of $R_{34}$, $R_{35}$ and $R_{36}$ is a hydrogen atom.

(6) polymers derived from the N-carboxyalkylation of chitosan, such as N-carboxymethylchitosan or N-carboxybutylchitosan, sold under the name EVALSAN by Jan Dekker.

(7) polymers corresponding to the general formula (XX) as are described, for example, in French Patent No. 1,400,366:

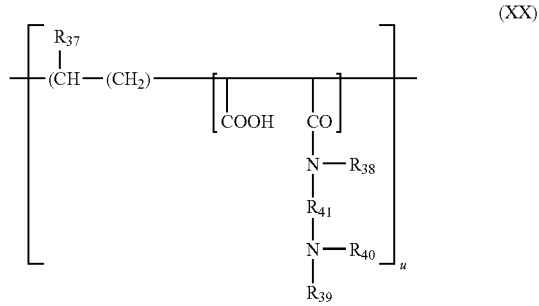

in which:

u is such that the molecular mass of the final polymer ranges from about 500 to about 5,000,000, e.g., from about 1000 to about 3,000,000.

$R_{37}$ is chosen from a hydrogen atom, a $CH_3O$ radical, a $CH_3CH_2O$ radical and a phenyl radical;

$R_{38}$ is chosen from a hydrogen and $C_1$-$C_4$ alkyl radicals such as methyl or ethyl;

$R_{39}$ is chosen from hydrogen and $C_1$-$C_4$ alkyl radicals such as methyl or ethyl;

$R_{40}$ is chosen from $C_1$-$C_4$ alkyl radicals such as methyl or ethyl and radicals corresponding to the formula: —$R_{41}$—N($R_{39}$)$_2$, wherein $R_{39}$ is defined above and $R_{41}$ is defined below;

$R_{41}$ is chosen from —$CH_2$—$CH_2$—, —$CH_2$—$CH_2$—$CH_2$— and —$CH_2$—$CH(CH_3)$— groups as well as the higher homologues of these radicals containing up to 6 carbon atoms.

(8) amphoteric polymers of the type -Y-Z-Y-Z chosen from:

a) polymers obtained by the action of chloroacetic acid or sodium chloroacetate on compounds containing at least one unit of formula:

-Y-Z-Y-Z-Y- where Y denotes a radical

and Z, which may be identical or different, may be chosen from T and T', wherein T and T', which may be identical or different, are chosen from divalent alkylene radicals containing a straight or branched chain containing up to 7 carbon atoms in the main chain, which is unsubstituted or substituted with hydroxyl groups and wherein said radicals may contain groups chosen from hydroxyl, benzylamine, amine oxide, quaternary ammonium, amide, imide, alcohol, ester, and urethane groups; at least one atom chosen from oxygen, nitrogen and sulphur atoms; and may further contain 1 to 3 aromatic and/or heterocyclic rings; the oxygen, nitrogen and sulphur atoms being present in the form of ether, thioether, sulphoxide, sulphone, sulphonium, alkylamine and alkenylamine groups;

b) polymers of formula:

-Y-Z-Y-Z in which Y denotes a radical

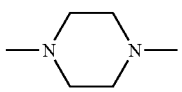

and Z, which may be identical or different, may be chosen from T and T', at least one occurrence of Z being T', wherein T is chosen from divalent alkylene radicals containing a straight or branched chain containing up to 7 carbon atoms in the main chain, which is unsubstituted or substituted with hydroxyl groups and wherein said radicals may contain groups chosen from hydroxyl, benzylamine, amine oxide, quaternary ammonium, amide, imide, alcohol, ester, and urethane groups; at least one atom chosen from oxygen, nitrogen and sulphur atoms; and may further contain 1 to 3 aromatic and/or heterocyclic rings; the oxygen, nitrogen and sulphur atoms being present in the form of ether, thioether, sulphoxide, sulphone, sulphonium, alkylamine and alkenylamine groups; and T' is chosen from divalent alkylene radicals with a straight or branched chain having up to 7 carbon atoms in the main chain, which is unsubstituted or substituted with one or more hydroxyl radicals, said radicals containing one or more nitrogen atoms, the nitrogen atom being substituted with an alkyl chain which is optionally interrupted by an oxygen atom, wherein T' necessarily contains at least one function chosen from carboxyl and hydroxyl functions and T' is betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

Among the amphoteric polymers which may be used according to the invention, one may, for example, use polymers of family (1).

The at least one amphoteric polymer is generally present in the inventive composition in an amount sufficient to provide improved styling to keratinous fibers, wherein the composition contains at least one compound chosen from ceramides and glycoceramides present in an amount effective for providing improved protection to keratinous fibers. In one embodiment, the at least one amphoteric polymer may be present in the inventive composition in an amount ranging from about 0.01 to about 5% by weight relative to the total weight of the composition. In another embodiment, the at least one amphoteric polymer is present in an amount ranging from about 0.05% to about 2% by weight relative to the total weight of the composition.

The composition of the present invention can also contain various adjuvants conventionally used in compositions for treating the hair, such as, but not limited to, surfactants chosen from anionic, cationic, nonionic, and amphoteric surfactants; polymers chosen from anionic, cationic, nonionic, and amphoteric polymers other than the cationic and amphoteric polymers discussed above; thickeners chosen from inorganic and organic thickeners; antioxidants; stabilizing agents; propellants; sequestering agents; emollients; humectants; fragrances; acidifying and basifying agents; sunscreens; vitamins; essential fatty acids; proteins and protein derivatives; preservatives; and opacifiers. Needless to say, a person skilled in the art will take care to select optional adjuvants such that the advantageous properties intrinsically associated with the invention are not, or are not substantially, adversely affected by the addition(s) envisaged.

The compositions of the present invention may be in a form chosen from an aqueous emulsion, a gel, a spray, an aerosol foam, a cream, and a hydroalcoholic lotion.

The present invention is also drawn to a process for protecting keratinous fibers, such as human hair, from damage caused by chemical treatments, such as permanent waving, relaxing, bleaching, and dyeing, by applying to the keratinous fibers a leave-in composition comprising at least one compound chosen from ceramides and glycoceramides, and then, without rinsing, applying to the keratinous fibers a chemical treatment composition. In one embodiment, the leave-in composition used in the inventive process further comprises at least one polymer chosen from at least one cationic polymer and at least one amphoteric polymer as described above.

The present invention is further drawn to a multi-compartment kit for chemical treatment of keratinous fibers, comprising at least two separate compartments, wherein a first compartment contains a composition comprising at least one compound chosen from ceramides and glycoceramides, and a second compartment contains a composition for chemical treatment of the keratinous fibers. In one embodiment, the first compartment may also contain at least one polymer chosen from at least one cationic polymer and at least one amphoteric polymer as described above.

The examples given below, purely by way of illustration and with no limiting nature, will allow the invention to be understood more clearly.

EXAMPLES

Example 1

Relaxer Pre-Treatment

A pre-treatment composition having the following ingredients was applied by a cosmetologist to half a head of hair and distributed evenly. It was noted that the composition had a good feel, was easy to distribute and gave the hair a good feel as well. The other half head was not treated. The pre-treatment was applied to seven (7) subjects in this manner.

| INGREDIENT | % ACTIVE MATERIAL |
|---|---|
| 2-oleamido-1,3-octadecanediol (sold as MEXANYL GZ by Chimex) | 0.001 |
| Hexadimethrine Chloride (sold as IONENE G (Chimex), 60% soln in water) | 1 |
| Polyquaternium-22 (sold as MERQUAT-280 (Calgon), 40% soln in water) | 0.75 |
| Emulsifiers and surfactants | 2.6 |
| Emollients | 0.2 |
| Humectants | 3 |
| Sequestering Agent | 0.15 |
| Preservatives | 1 |
| Thickening Agent | 0.75 |
| pH adjusting agent | q.s. to pH 4.6 ± 0.3 |
| Fragrance | 0.5 |
| Water | q.s. to 100 |

Without rinsing the hair, the cosmetologist applied a relaxer composition to the entire head of each subject and left the composition on the head for a time sufficient to relax the hair as desired. The hair was then rinsed thoroughly, washed with a neutralizing shampoo, rinsed again, and styled. The hair was evaluated before and after the washing step.

Before shampooing, the relaxed hair with the pre-treatment was found to have a smoother feel and better combability. After shampooing, the relaxed, pre-treated hair was found to have better combability, smoother cuticle, softer feel, and a higher level of sheen than the untreated hair. The results are shown in the table below. The evaluations, performed by skilled cosmetologists, were based on a rating system of 1 to 5, where 1=poor, 2=fair, 3=good, 4=very good and 5=excellent). The numbers listed below are averages based on actual readings for the 7 heads obtained during testing. Any difference in value equal to or less than ±0.3 is not considered a significant difference in value.

| | WITH PRE-TREATMENT | WITHOUT PRE-TREATMENT |
|---|---|---|
| DURING and AFTER RINSING RELAXER but BEFORE SHAMPOO | | |
| WET FEEL UNDER WATER | 4 | 3.4 |
| WET HAIR FEEL | 4.2 | 3.4 |
| DETANGLING | 3.8 | 3.2 |
| SMOOTHNESS | 3.9 | 3.3 |
| HAIR AFTER USING NEUTRALIZING SHAMPOO | | |
| WET HAIR FEEL | 4.2 | 3.6 |
| DETANGLING | 4.3 | 3.6 |
| SMOOTHNESS | 4.3 | 3.7 |
| SOFTNESS | 4.3 | 3.6 |
| SHEEN | 3.8 | 3.3 |

Example 2

Permanent Hair Color Pre-Treatment

The pre-treatment composition of Example 1, except without the 0.50% fragrance, was applied to half a head of hair by a cosmetologist and distributed evenly. It was noted that the composition applied easily through the hair. The other half head was not treated. Three (3) subjects' heads were prepared in this manner.

Without rinsing the hair, the cosmetologist applied a permanent hair color composition (oxidation dye) to the entire head and left it on for at least 30 minutes to obtain the color desired. The hair was then rinsed thoroughly until the rinse water ran clear, then washed with a cleansing shampoo, rinsed again, and dried. The hair was evaluated before shampooing and after drying.

After shampooing, the dyed hair with the pre-treatment was found to have significantly improved properties of wet hair detangling, smoothness of wet hair, and wet hair feel. After drying, the dyed, pre-treated hair was found to have better properties of static, smoothness of dry hair, dry hair feel, ease of setting/styling, hair resiliency, hair manageability, and shine compared to the hair that was not pre-treated. The results are shown in the table below. The evaluations, performed by skilled cosmetologists, were based on a rating system of 1 to 5, where 1=poor, 2=fair, 3=good, 4=very good and 5=excellent). The numbers listed below are averages based on actual readings for the 3 heads obtained during testing. Any difference in value less than ±0.5 is not considered a significant difference in value.

| | WITH PRE-TREATMENT | WITHOUT PRE-TREATMENT |
|---|---|---|
| HAIR AFTER RINSING COLOR BUT BEFORE SHAMPOO | | |
| WET HAIR DETANGLING | 3 | 3.3 |
| SMOOTHNESS OF WET HAIR | 3.3 | 2.7 |
| WET HAIR FEEL | 3.3 | 3.3 |
| WET HAIR SOFTNESS | 3.3 | 3.3 |
| HAIR AFTER SHAMPOO | | |
| WET HAIR DETANGLING | 3.7 | 3 |
| SMOOTHNESS OF WET HAIR | 3.7 | 3 |
| WET HAIR FEEL | 3.3 | 2.7 |
| HAIR SOFTNESS | 3 | 3.3 |
| HAIR AFTER DRYING | | |
| DRY HAIR DETANGLING | 3.3 | 3.3 |
| STATIC | 4.7 | 3.7 |
| SMOOTHNESS OF DRY HAIR | 4 | 3.7 |
| DRY HAIR FEEL | 3.7 | 3.3 |
| EASE OF SETTING/STYLING | 3.7 | 3 |
| VISUAL VOLUME | 3.3 | 3 |
| HAIR RESILIENCY | 4 | 3 |
| HAIR MANAGEABILITY | 3.7 | 3 |
| SHINE | 4 | 3.3 |
| DRY HAIR SOFTNESS | 3.3 | 3 |

Example 3

Pre-Treatment Composition

The following pre-treatment composition was formulated for use as a leave-in composition prior to chemical treatment of hair.

| INGREDIENT | % ACTIVE MATERIAL |
|---|---|
| 2-oleamido-1,3-octadecanediol (sold as MEXANYL GZ by Chimex) | 0.001 |
| Hexadimethrine Chloride (sold as IONENE G (Chimex), 60% soln in water) | 0.3 |

-continued

| INGREDIENT | % ACTIVE MATERIAL |
|---|---|
| Polyquaternium-22 (sold as MERQUAT-280 (Calgon), 40% soln in water) | 0.15 |
| Emulsifiers and surfactants | 5.2 |
| Emollients | 0.05 |
| Humectants | 3 |
| Preservatives | 1 |
| Sequestering Agent | 0.06 |
| pH adjusting agent | q.s. to pH 4.6 ± 0.3 |
| Fragrance | 0.5 |
| Water | q.s. to 100 |

Example 4

Pre-Treatment Composition

The following pre-treatment composition was formulated for use as a leave-in composition prior to chemical treatment of hair.

| INGREDIENT | % ACTIVE MATERIAL |
|---|---|
| 2-oleamido-1,3-octadecanediol (sold as MEXANYL GZ by Chimex) | 0.001 |
| Hexadimethrine Chloride (sold as IONENE G (Chimex), 60% soln in water) | 0.06 |
| Polyquaternium-22 (sold as MERQUAT-280 (Calgon), 40% soln in water) | 0.03 |
| Emulsifiers and surfactants | 3.7 |
| Emollients | 0.05 |
| Humectants | 3 |
| Preservatives | 1 |
| Sequestering Agent | 0.06 |
| pH adjusting agent | q.s. to pH 4.6 ± 0.3 |
| Water | q.s. to 100 |

The foregoing written description relates to various embodiments of the present invention. Numerous changes and modifications may be made therein without departing from the spirit and scope of the invention as defined in the following claims.

What is claimed is:

1. A composition for the protection of keratinous fibers, said composition comprising:
(i) at least one compound chosen from ceramides and glycoceramides of formula (I):

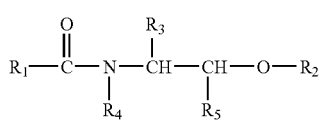

(I)

wherein:
R$_1$ is chosen from optionally hydroxylated, saturated or unsaturated alkyl radicals derived from C$_{14}$-C$_{22}$ fatty acids;
R$_3$ is chosen from optionally hydroxylated linear, saturated C$_{11}$-C$_{17}$ radicals; and
R$_2$, R$_4$, and R$_5$ hydrogen, (ii) at least one cationic polymer chosen from
polymers comprising repeating units corresponding to Formula IX:

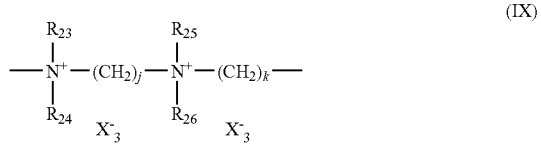

wherein:
R$_{23}$, R$_{24}$, R$_{25}$ and R$_{26}$ are each independently chosen from C$_1$-C$_4$ alkyl radicals and C$_1$-C$_4$ hydroxyalkyl radicals;
j and k are integers ranging from 2 to 20; and
X$^-_3$ is an anion chosen from inorganic and organic acids; and

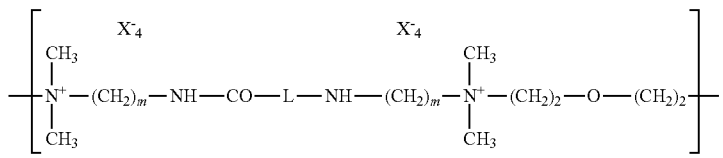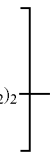

(iii) at least one amphoteric polymer resulting from the copolymerization of at least one monomer derived from at least one vinyl compound bearing a carboxylic group and at least one monomer derived from a dialkyldiallylammonium salt;
wherein the at least one compound chosen from ceramides and glycoceramides is present in the composition in an amount ranging from about 0.001% to about 1% by weight relative to the total weight of the composition,
wherein the at least one cationic polymer is present in the composition in an amount ranging from about 0.01% to about 5% by weight relative to the total weight of the composition, and
wherein the at least one amphoteric polymer is present in the composition in an amount ranging from about 0.01% to about 5% by weight relative to the total weight of the composition.

2. A composition according to claim 1, wherein R$_3$ is an optionally hydroxylated linear, saturated C$_{13}$-C$_{15}$ radical.

3. A composition according to claim 1, wherein the at least one compound chosen from ceramides and glycoceramides is chosen from:
N-linoleoyldihydrosphingosine,
N-palmitoyldihydrosphingosine,
N-stearoyldihydrosphingosine,
N-behenoyldihydrosphingosine,
N-2-hydroxypalmitoyldihydrosphingosine,
N-stearoylphytosphingosine,
2-oleamido-1,3-octadecanediol, and
N-palmitamidohexadecanediol.

4. A composition according to claim 3, wherein the at least one compound chosen from ceramides and glycoceramides is chosen from 2-oleamido-1,3-octadecanediol and N-2-hydroxypalmitoyldihydrosphingosine.

5. A composition according to claim 1, wherein the at least one cationic polymer is chosen from polyquaternium-34 and hexadimethrine chloride.

6. A composition according to claim 1, further comprising at least one adjuvant chosen from surfactants chosen from anionic, cationic, nonionic, and amphoteric surfactants; polymers chosen from anionic, nonionic, additional cationic and additional amphoteric polymers; thickeners chosen from inorganic and organic thickeners; antioxidants; stabilizing agents; propellants; sequestering agents; emollients; humectants; fragrances; acidifying and basifying agents; sunscreens; vitamins; essential fatty acids; proteins and protein derivatives; preservatives; and opacifiers.

7. A composition according to claim 1, wherein the composition is in the form of an aqueous emulsion, a gel, a spray, or a hydroalcoholic lotion.

8. A composition according to claim 1, wherein the at least one amphoteric polymer is chosen from polyquaternium-22 and polyquaternium-39.

9. A multi-compartment kit for chemical treatment of keratinous fibers, the kit comprising at least two separate compartments, wherein
a first compartment comprises a cosmetic composition comprising
(i) least one compound chosen from ceramides and glycoceramides of formula (I):

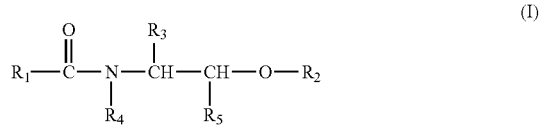

wherein:
R$_1$ is an optionally hydroxylated, saturated or unsaturated alkyl radical derived from C$_{14}$-C$_{22}$ fatty acids;
R$_3$ is an optionally hydroxylated linear, saturated C$_{11}$-C$_{17}$ radical; and
R$_2$, R$_4$, and R$_5$ are hydrogen,
(ii) at least one cationic polymer chosen from
polymers comprising repeating units corresponding to Formula IX:

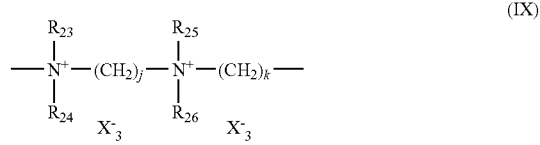

wherein:
R$_{23}$, R$_{24}$, R$_{25}$ and R$_{26}$ are each independently chosen from C$_1$-C$_4$ alkyl radicals and C$_1$-C$_4$ hydroxyalkyl radicals;
j and k are integers ranging from 2 to 20; and
X$^-_3$ is an anion chosen from inorganic and organic acids; and

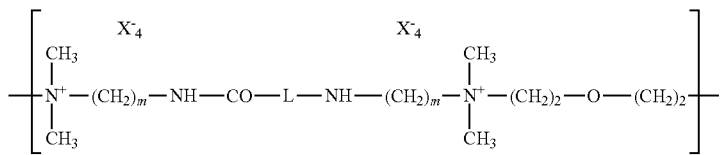

(iii) at least one amphoteric polymer resulting from the copolymerization of at least one monomer derived from at least one vinyl compound bearing a carboxylic group and at least one monomer derived from a dialkyldiallylammonium salt, and a second compartment comprises a composition for chemical treatment of the keratinous fibers, wherein the composition for chemical treatment is an oxidizing composition;

wherein the at least one compound chosen from ceramides and glycoceramides is present in the cosmetic composition in an amount ranging from about 0.001% to about 1% by weight relative to the total weight of the cosmetic composition, wherein the at least one cationic polymer is present in the cosmetic composition in an amount ranging from about 0.01% to about 5% by weight relative to the total weight of the cosmetic composition, and wherein the at least one amphoteric polymer is present in the cosmetic composition in an amount ranging from about 0.01% to about 5% by weight relative to the total weight of the cosmetic composition.

10. A multi-compartment kit according to claim 9, wherein the composition for chemical treatment of keratinous fibers is chosen from a dyeing composition, a bleaching composition, a permanent waving composition, and a relaxing composition.

11. A multi-compartment kit according to claim 9, wherein the at least one amphoteric polymer is chosen from polyquaternium-22 and polyquaternium-39.

* * * * *